US011065458B2

(12) United States Patent
Mehnert et al.

(10) Patent No.: US 11,065,458 B2
(45) Date of Patent: Jul. 20, 2021

(54) ELECTRONIC PACEMAKER

(71) Applicants: Walter Mehnert, Ottobrunn (DE);
Thomas Theil, Feldafing (DE)

(72) Inventors: Walter Mehnert, Ottobrunn (DE);
Thomas Theil, Feldafing (DE)

(*) Notice: Subject to any disclaimer, the term of this patent is extended or adjusted under 35 U.S.C. 154(b) by 98 days.

(21) Appl. No.: 16/250,303

(22) Filed: Jan. 17, 2019

(65) Prior Publication Data
US 2019/0217108 A1 Jul. 18, 2019

(30) Foreign Application Priority Data

Jan. 17, 2018 (DE) ...................... 10 2018 100 998.4
Apr. 18, 2018 (DE) ...................... 10 2018 205 940.3

(51) Int. Cl.
*A61N 1/375* (2006.01)
*A61N 1/05* (2006.01)
(Continued)

(52) U.S. Cl.
CPC ....... *A61N 1/37512* (2017.08); *A61N 1/0529* (2013.01); *A61N 1/3752* (2013.01);
(Continued)

(58) Field of Classification Search
CPC .............. A61N 1/37512; A61N 1/3787; A61N 1/0529; A61N 1/3752; A61N 1/362;
(Continued)

(56) References Cited

U.S. PATENT DOCUMENTS 3,820,090 A 6/1974 Wiegand
6,505,077 B1 1/2003 Kast et al.

FOREIGN PATENT DOCUMENTS

DE 10127807 A1 3/2002
DE 102006062541 A1 8/2007
(Continued)

OTHER PUBLICATIONS

Communication dated Oct. 29, 2018 issued by the German Patent and Trademark Office in counterpart application No. 10 2018 205 940.3.
(Continued)

*Primary Examiner* — Mark Bockelman
(74) *Attorney, Agent, or Firm* — Sughrue Mion, PLLC

(57) ABSTRACT

An electronic pacemaker for implantation in a body of a living being including an electrode portion that is configured to be attached to a body portion; an electronics assembly connected with the electrode portion, configured to generate a voltage impulse emitted via the electrode portion to the body portion; a rechargeable accumulator to supply the electronics assembly with electrical energy; and a charging impulse generation portion electrically connected to the accumulator, configured to emit a charging impulse to the accumulator for the recharging of the accumulator. The charging impulse generation portion includes a magnetization portion with oriented magnetic domains which can be contactlessly influenced by an changing magnetic field so that, when a certain field strength is reached, a remagnetization wave, caused by the continuously reversing magnetic domains, occurs in the magnetization portion which runs across the magnetization portion and leads to the generation of the charging impulse.

15 Claims, 3 Drawing Sheets

(51) Int. Cl.
*A61N 1/378* (2006.01)
*A61N 1/362* (2006.01)

(52) U.S. Cl.
CPC ............ *A61N 1/3787* (2013.01); *A61N 1/057* (2013.01); *A61N 1/362* (2013.01)

(58) Field of Classification Search
CPC ........ A61N 1/057; A61N 1/372; A61N 1/378; H02J 50/10; H02J 7/025
See application file for complete search history.

(56) References Cited

FOREIGN PATENT DOCUMENTS

WO 2012/013212 A1 2/2012
WO 2012/150000 A2 11/2012

OTHER PUBLICATIONS

A. Matsushita et al., "Power generating device using compound magnetic wire", Journal of Applied Physics, America Institute of Physics, vol. 87, No. 9, pp. 6307-6309, May 1, 2000, 3 pages total.
Stefano Saggini et al., "Low-Power Energy Harvesting Solutions for Wiegand Transducers", IEEE Journal of Emerging and Selected Topics in Power Electronics, vol. 3, No. 3, pp. 766-779, Sep. 2015, 14 pages total.
Extended European Search Report dated Jun. 25, 2019 issued by the European Patent Office in counterpart application No. 19152333.1.

ELECTRONIC PACEMAKER

The invention relates to an electronic pacemaker for implantation into a body of a living being.

Pacemakers that are fully implanted into the human body as intended are generally known in prior art and are used for various different medical indications.

Pacemakers are used, for example, as so-called cardiac pacemakers for human heart diseases. The main components of a cardiac pacemaker form the electrodes that are attached to the patient's diseased heart, and an electronics assembly which, when it detects heart malfunctions, emits stimulation impulses to the heart via said electrodes. Currently, permanent cardiac pacemakers are fully implanted into the human body.

Other types of pacemakers are, for example, bladder pacemakers or brain pacemakers which have electrodes as well via which a corresponding electronics assembly emits stimulation Impulses to the brain or nerve tracts.

What all types of pacemakers have in common is that they have a battery to provide the electronics assembly with electric energy. These batteries are, however, the weak point of the known pacemakers because, due to the limited available space, the available energy content of the batteries limits their useful life. But, especially, such pacemakers should operate the whole life. Self-discharge and a high electricity demand require that the batteries are replaced. The replacement of the battery is, however, associated with a surgical procedure and must therefore be considered unfavorable.

A single-chamber cardiac pacemaker of the latest generation, which stimulates one of the ventricles through an electrode, may, due to its size, be slid directly into the corresponding ventricle and anchored there directly in the myocardium by means of its multi-arm electrode. When the battery is empty in this single-chamber cardiac pacemaker, another is inserted into the heart that takes over the required stimulation. The first single-chamber cardiac pacemaker remains ingrown in the heart and is not or cannot respectively, be removed again.

It is difficult and/or almost impossible to recharge the pacemaker's battery wirelessly by induction because the penetration depth of electromagnetic fields with a power transmission required for the recharging is too low at high frequencies, especially if these fields have to penetrate a metal case that is necessary, for example for EMC reasons.

Against the above background, it is an object of the present invention to provide an electronic pacemaker with an improved energy supply.

This object is achieved by an electronic pacemaker according to claim 1. Preferred embodiments are the subject matter of the dependent claims.

According to an aspect of the invention, an electronic pacemaker is provided in accordance with the intended use, for implanting into a body of a living being and controlling a bodily function.

The electronic pacemaker according to the invention may be for example a cardiac pacemaker (single-chamber cardiac pacemaker, dual-chamber cardiac pacemaker, and triple-chamber cardiac pacemaker), a brain pacemaker, or an intestinal pacemaker. The electronic pacemaker according to the invention is fully implanted into the body of the living being, in particular a human body.

The electronic pacemaker according to the invention comprises an electrode portion that is, according to its intended use, to be electroconductively attached to a body portion. The electrode portion comprises a certain number of electrodes, depending on the purpose of the electronic pacemaker and/or the body function it is to stimulate. The electrodes are, in accordance with the intended use, connected with the body portion to be stimulated, e.g., the heart or the brain.

If the electronic pacemaker according to the invention is, for example, a single-chamber cardiac pacemaker, it comprises a single electrode which is connected with the half of the heart to be stimulated, for example the atrium or the ventricle. If the electronic pacemaker according to the invention is, however, a dual-chamber cardiac pacemaker, it comprises two electrodes which are connected with the half of the heart to be stimulated, for example the atrium or the ventricle. The electrodes comprise, for example at their ends, spiral segments which are twisted into the myocardium and thus anchored in it.

In general, the electronic pacemaker according to the invention may be a cardiac pacemaker according to any NBG code.

In general, the electrodes mentioned may be cable electrodes, for example. In particular, the pacemaker preferably comprises in this context one cable of a certain length per cable electrode which cable, according to the intended purpose, may be guided to a desired area of the body portion within the body. The preferably spiral segment used to anchor the cable electrode in the area of the body portion is formed at the end of the cable.

Alternatively, the pacemaker and/or the electrode portion can do without cable electrode(s) as well. In this case, said electrodes are formed on an outer surface of the pacemaker, wherein the pacemaker is implanted so that the electrodes can touch an area of the body portion and/or be anchored there. If the pacemaker has a plurality of electrodes formed on the outer surface, the pacemaker has the corresponding dimensions so that the electrodes formed on the outer surface can touch the respective area of the body portion and/or be anchored there.

In a further alternative, the electrode portion may be composed of a combination of at least a single cable electrode and of at least a single electrode formed on the outer surface. In this case, the pacemaker is preferably arranged at the body portion so that the electrode formed on the outer surface comes in contact with the corresponding area of the body portion and/or is anchored there. The other electrode, i.e., the cable electrode, is guided to another area of the body portion and anchored or attached there.

Generally speaking, the electrode portion of the electronic pacemaker according to the invention comprises a plurality of electrodes necessary for the medical indication.

Furthermore, the electronic pacemaker according to the invention comprises an electronics assembly connected with the electrode portion, which is configured to generate an impulse (stimulation impulse or voltage impulse) according to captured body data, and to emit the same via the electrode portion to the body portion for controlling the bodily function.

The electronics assembly of the electronic pacemaker according to the invention is preferably configured to monitor the bodily function to be stimulated or controlled to capture the body data and, if necessary, to emit the impulse (stimulation impulse or voltage impulse) via the electrode portion to the body portion.

Depending on the purpose and type of the electronic pacemaker according to the invention, the electronics assembly may generate the impulse continuously or as needed when a malfunction of the body is detected and emit it via the electrode portion.

If the electronic pacemaker according to the invention is a cardiac pacemaker, the electronics assembly may preferably be configured to comprise one or more functions (operating modes and/or frequency adaptation) according to the NBC pacemaker code.

Furthermore, the electronic pacemaker according to the invention comprises an energy storage, for example an accumulator or a capacitor (for example a gold cap) to supply the electronics assembly with electrical energy, which can be recharged with electrical energy after discharge.

The type of energy storage of the electronic pacemaker according to the invention may be chosen at will. The energy storage may, for example, be an accumulator, preferably a rechargeable lithium-ion accumulator. Alternatively, the energy storage may be a capacitor with a preferably low self-discharge. The energy storage may preferably be hermetically encapsulated so that it does not present any danger to the body of the living being.

According to the invention, the electronic pacemaker comprises a charging impulse generation portion electrically connected to the energy storage, which is configured to be able to emit a charging impulse for the recharging of the energy storage, wherein the charging impulse generation portion comprises a magnetization portion with oriented magnetic domains, which can be contactlessly influenced by an changing (external) magnetic field so that, when a certain field strength (amplitude) is reached, a remagnetization wave, caused by the continuously reversing magnetic domains, occurs in the magnetization portion which runs across the magnetization portion and leads to the generation of the charging impulse.

The mentioned external or externally generated magnetic field is preferably generated by the charging device according to the invention, which will be explained below.

The magnetization portion of the charging impulse generation portion comprises equally oriented magnetic domains which, together, can be influenced by the changing externally generated magnetic field. When the externally generated magnetic field reaches in a certain area of the magnetization portion a certain amplitude or field strength that is in the range of a few millitesla (less than or equal to 10 mT), the domains reverse their magnetization polarity in this area (reversal of the so-called Weiss domains), whereby said remagnetization wave starts running across the magnetization portion, as is the case for example in a Wiegand or impulse wire still to be mentioned below.

The form of the magnetization portion is arbitrary.

When the strength of the externally generated magnetic field reaches, for example at one end of the magnetization portion, the certain amplitude or strength, the remagnetization wave begins to run at this end of the magnetization portion until it reaches the other end of the magnetization portion. From a physical perspective, this thus occurring remagnetization wave is essentially a Bloch wail that runs across the magnetization portion.

The remagnetization of the magnetization portion is used to generate the charging impulse, for example by induction.

It should be specifically mentioned here that the size (amplitude) and the speed of the remagnetization wave does not depend, or only insignificantly, on the frequency of the changing externally generated magnetic field, but primarily on the material data of the magnetization portion. The trigger point of the remagnetization wave depends on when the changing externally generated magnetic field reaches the mentioned amplitude or field strength, wherein the gradient of the change of the magnetic field and the corresponding frequency, respectively, does not play a role. When the necessary strength (amplitude) of the magnetic Reid is reached, the Bloch wall and the remagnetization wave, respectively, begins to run.

The commutation frequency or the change of the magnetic field only play a role, albeit a subordinate role, because it only provides information about the number of the initiations of the remagnetization wave or it only indicates, respectively, how often the remagnetization wave is initiated and therefore how often a charging impulse is generated.

The electronic pacemaker according to the invention is preferably configured so that the charging impulse generation portion comprises at least one coil, which is spatially arranged to the magnetization portion so that it generates a voltage impulse, which leads to a charging impulse, when the remagnetization wave occurs.

The spatial arrangement may be such that the coil is wound around the magnetization portion, and in particularly that it axially surrounds the same.

It is common knowledge that coils made from electrically conductive materials are inductances. The remagnetization wave causes the coil, due to its inductive properties, to generate the voltage impulse that leads to the charging impulse.

For each commutation of the alternating magnetic field, the coil therefore generates a voltage impulse of a certain strength (independently from how quickly or with which frequency the magnetic field changes). The magnetization portion and the coil may, for example, be dimensioned so that the amplitude of the voltage impulse that leads to the charging impulse is 10V or higher.

The voltage impulses generated by the coil have alternating reversed polarities. To use all voltage impulses, the charging impulse generation portion comprises charging electronics that preferably rectify the voltage impulses by means of a rectifier and/or temporarily store them in a capacitor.

In general terms, the advantage of the invention is that a part of the magnetic energy of the alternating magnetic field first accumulates in the magnetization portion and is then quite suddenly released in the form of the moving remagnetization wave. The induction and therefore the creation of the electrical voltage consequently occurs on/in the coil at this point in time at first. This means that the contactless energy transmission is not based on the fact that the alternating magnetic field is used immediately for the voltage induction in the coil, but that the corresponding enemy of the magnetic field is temporarily stored in the magnetization portion and then released quite suddenly when the remagnetization wave is initiated. For this reason, the commutation frequency may be adapted so that energy can be transmitted through a case or sleeve made from metal without any problems According to the invention, it is an indirect induction method; the change of the magnetic flux generated by the electricity of the primary coil does not exclusively lead to voltage in the secondary coil, as is the case with the direct induction, but part of this flux is initially temporarily stored in the magnetization portion. At a certain field strength, the flux then stimulates the magnetization portion to generate a magnetic impulse wave of a certain polarity (remagnetization wave) and therefore indirectly In the secondary coil a voltage impulse of a certain polarity with a significantly higher amplitude. The coil of the charging impulse generation portion acts here as said secondary coil that generates the voltage Impulse when the remagnetization wave occurs. Said primary coil is located for example in the charging device to be explained below.

In this point, the Invention differs significantly from known contactless charging processes for accumulators which use an electromagnetic alternating field for the transmission of energy. Such an electromagnetic alternating field with a high frequency can hardly or at least very difficultly be used in pacemakers to be implanted because the penetration depth of the electromagnetic alternating field into the body of the living being, particularly into a metal case, is too low due to the effects that occur such as, for example, the skin effect.

The magnetization portion of the electronic pacemaker according to the invention is preferably configured, due to a special, e.g., mechanical, machining, so that the magnetic domains of the magnetization portion are equally oriented.

The magnetization portion of the electronic pacemaker according to the invention preferably comprises a magnetically hard shell area which encloses a magnetically soft core area, The magnetically hard shell is created for example when the magnetization portion is machined and produced. A preferred material for the magnetization portion is vicalloy, which is machined for example in cold forming steps to orient the magnetic domains.

Preferably, the magnetization portion is at least an impulse wire or a Wiegand wire. The magnetization portion may also comprise a plurality of impulse wires or a plurality of Wiegand wires or a combination of at least one impulse wire and one Wiegand wire.

The number of the coils is not limited to a single coil as well. Each of the wires may be assigned a coil of its own, or, alternatively, a plurality of the wires may be surrounded by one or more coils. Preferably, the coil is, or the coils are, wound around one or more of the wires.

In this case, the cons each form a secondary coil of the indirect induction method explained above, to which energy is indirectly transmitted via the magnetization portion from the primary coil, which is preferably located in the charging device still to be explained.

Preferably, the electronic pacemaker according to the invention is formed so that the electronics assembly together with the energy storage and the charging impulse generation portion are fully surrounded by a sleeve or a case which is made from a material that is not rejected by the body of the living being. The material is preferably a non-ferromagnetic metal, in particular titanium, or a metal alloy comprising titanium in particular. Alternative metals are stainless steels. The electric conductivity of these materials is important to dampen high-frequency interfering fields that may impair the function of the pacemaker, for example of the cardiac pacemaker.

The electrically conducting case may also be required or may serve as a mass contact, in order to close the current circuit via the electrode(s). The mass contact may be alternatively formed by an electrically conductive portion, which is exposed on an outer surface of a potentially not entirely electrically conductive case. Further, the mass contact may be a separate mass (cable) electrode.

The electrode portion and/or the mass contact is/are, for example, detachable from the sleeve or the case and runs through the same respectively, and is/are connected with the electronics assembly inside the sleeve/case.

As described above, the electrodes and/or the mass contact may be cable electrodes or electrodes formed on the outer surface. The outer surface is, in particular, an outer surface of the sleeve/case.

Overall, the sleeve/case can, together with the accommodated elements, the corresponding electrode portion, and the mass contact be formed so small that the pacemaker, for example in the embodiment of the cardiac pacemaker, can be implanted in the heart, for example directly in the myocardium or attached to the outside of the heart.

This significant miniaturization potential compared to prior art is due to the fact that the energy storage of the pacemaker that has already been explained does not have to be configured/dimensioned for a useful life of several years, but, because it is easy to recharge, can be much smaller. This reduces at the same time the risk potential, for example for the occurrence of a short circuit in the energy storage.

The fact that was already mentioned, that the magnetization portion accumulates the magnetic energy and only its release in the form of the remagnetization wave leads to the generation of the induced electrical voltage and the voltage impulse, respectively, within the case and the sleeve, respectively, creates freedom for the selection of the preferably non-ferromagnetic material of said sleeve and case, respectively, because no direct requirements as to the transmission frequency must be met Preferably, the charging impulse generation portion of the pacemaker according to the invention comprises, in a direction in which the at least one coil is wound or in which the coils ate wound, a magnetic collecting lens at least one end portion of the magnetization portion for bundling and guidance of the changing externally generated magnetic field to the magnetization portion.

Said direction corresponds to the longitudinal direction of the coil or the coils in which it is wound/they are wound Preferably, at least one magnetic collecting lens is arranged at both end portions of the magnetization portion, which bundle the changing externally generated magnetic field on the magnetization portion and/or lead it to the same.

Alternatively to the use of an independent collecting lens/collecting lenses, there is also the possibility that the sleeve and the case, respectively, partially or sectionally formed from ferromagnetic material or is partially or sectionally coated with such a material and, for example by a separation into two separate halves, is configured to directly take up the function of the magnetic collecting lenses. Due to the then larger configuration of the collecting lenses, the magnetic field to be generated by the charging device can then be reduced further.

The at least one magnetic collecting lens of the electronic pacemaker is preferably formed from ferromagnetic material which bundles the externally generated magnetic field for the magnetization portion.

The magnetic collecting lens(es) is/are made for example from ferrite and have, for example, the form of a hollow cylinder, the axis of which points in the direction of the respective end portion of the magnetization portion.

The magnetization portion is preferably inserted into the hollow cylinder.

The use of the magnetic collecting lens(es) makes it possible, for example, that the charging device still to be explained below can generate a lower magnetic field.

The electronics assembly of the electronic pacemaker according to the invention preferably does not comprise any elements from ferromagnetic materials, and/or the charging impulse generation portion of the electronic pacemaker according to the invention does not comprise any elements from ferromagnetic materials except for the magnetization portion, and, when preferably provided, the at least one collecting lens.

This configuration of the electronic pacemaker according to the invention is preferable in that the elements formed from non-ferromagnetic materials are not impaired or interfered with by the externally generated magnetic field.

It is furthermore preferred that the electronics assembly of the electronic pacemaker according to the invention is configured to send out a signal that indicates the quality of the charging impulse.

Said signal may, for example, be a low-frequency signal that penetrates the body of the living being and, if no respective antenna is provided, the sleeve or the case of the pacemaker according to the invention.

The quality of the charging impulse is determined, for example, by how strong the charging impulse is. The signal indicating the quality of the charging impulse may be a binary signal, for example, which assumes an OK state when the charging impulse exceeds a threshold and an NG state when the charging impulse does not exceed the threshold. Alternatively, said signal may also indicate the exact strength of the charging impulse.

The invention also relates to a charging device for an electronic pacemaker, wherein the charging device is configured to generate a magnetic field that changes with a commutation frequency and amplitude. If used as intended, the charging device is temporarily arranged on a body surface of the living being or close to the body surface of the living being so that the magnetic field penetrates the body and the implanted electronic pacemaker according to the invention to influence the charging impulse generation portion.

The commutation frequency preferably ranges from X to 10 kHz, wherein X>0 and X>=0.1 kHz, 0.2 kHz, 0.3 kHz, . . . , 4.9 kHz, . . , 9.9 kHz.

The charging device comprises for example one or a plurality of coils that act in the indirect induction method referred to above as the primary coil(s). It is preferred that a core, for example made from ferrite, is inserted into the coil(s).

As intended, the charging device generates a flow of electricity through the coil(s) to develop a changing electromagnetic field that commutes with the mentioned commutation frequency. When the charging device is arranged on the body surface and in its vicinity, respectively, the alternating field can penetrate the body of the living being and a pacemaker according to the invention, for example a cardiac pacemaker, arranged therein. The magnetic portion of the changing electromagnetic field forms the externally magnetic field explained above, which influences the magnetization portion for the initiation of the remagnetization wave.

The strength and/or the commutation frequency of the electromagnetic alternating field could preferably be controlled in the charging device. This is preferable in that the charging device may be adjusted depending on the location of the pacemaker within the body and the necessary penetration depth, respectively.

Preferably, the charging device according to the invention comprises a plurality of coils for the generation of the changing magnetic field, wherein the plurality of coils can be controlled accordingly on the basis of the signal indicating the quality of the charging impulse, for an optimization of the charging impulse.

The coils of the plurality of coils are preferably spatially arranged so that the charging device can adjust the orientation of the generated magnetic field by controlling the coils. This has the advantage that the charging device can adjust the orientation of the magnetic field in consideration of the signal indicating the quality of the charging impulse so as to improve or optimize the quality of the charging impulse.

The charging device is preferably configured to automatically control the coils for orienting of the magnetic field.

Below, a preferred embodiment of the invention is explained with reference to the figure.

FIG. 1 shows the schematic configuration of an electronic pacemaker 1 according to the invention.

Figure 1:
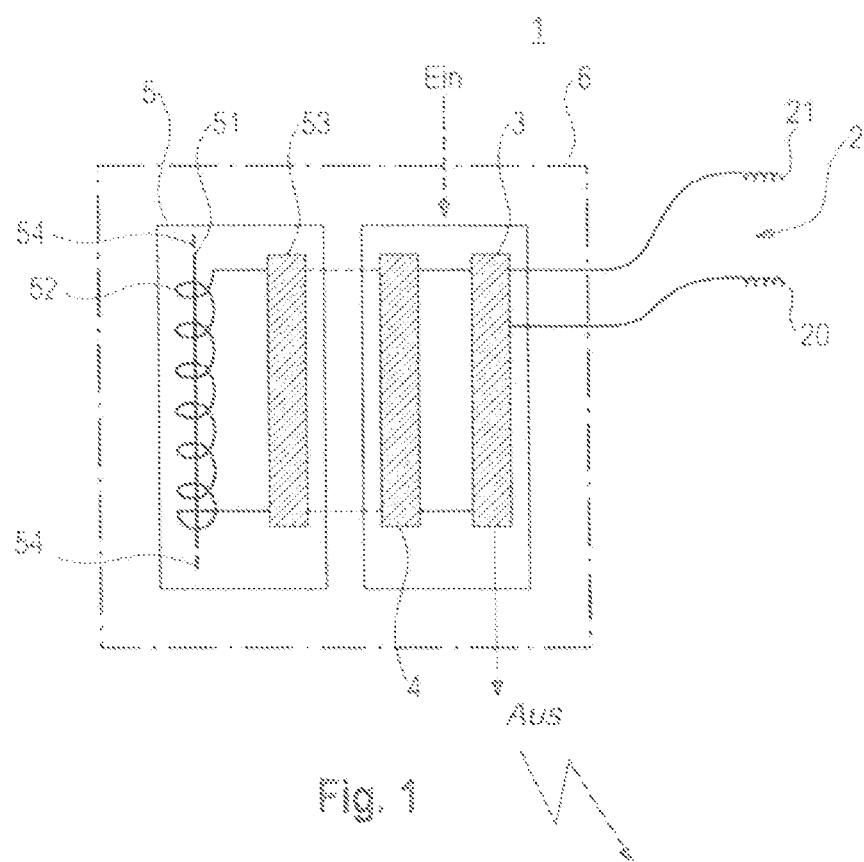
FIG. 1 shows a schematic illustration of an implant pacemaker according to the invention.

The electronic pacemaker 1 is a cardiac pacemaker in this preferred embodiment which, as intended, is completely implanted into the human body. The invention is not, however, limited to a cardiac pacemaker. The electronic pacemaker 1 may, for example, be a brain pacemaker or an intestinal pacemaker as well.

The cardiac pacemaker 1 comprises an electrode portion 2, which comprises, in this preferred embodiment, two electrodes 20, 21. The cardiac pacemaker 1 is therefore a dual-chamber cardiac pacemaker configured to stimulate an atrium and a ventricle of one side of the heart by means of the electrodes 20, 21. To this purpose, one of the electrodes is connected to the atrium and the other of the electrodes to the corresponding ventricle.

The configuration of the dual-chamber cardiac pacemaker is only preferred. Alternatively, the cardiac pacemaker may also be a single-chamber or triple-chamber cardiac pacemaker, wherein it then comprises the number of electrodes required for this purpose.

The electrode portion 2 is connected to an electronics assembly 3. The electronics assembly 3 is configured to take over the necessary functions of the cardiac pacemaker. The electronics assembly 3 receives an input signal Ein and body data, respectively, through which the cardiac pace maker and the electronics assembly 3, respectively, can detect whether the bodily function to be monitored or controlled (heartbeat) must be stimulated and controlled, respectively. When the electronics assembly 3 detects, for example, that there is no heartbeat after a certain time interval, it generates an impulse and stimulation impulse (current and/or voltage impulse), respectively, which is emitted to the atrium and/or the ventricle by means of the electrode portion 2 to stimulate the heart.

The electronics assembly 3 is preferably configured to generate the impulse and stimulate the heart only when needed.

The cardiac pacemaker 1 comprises an electrical energy storage 4, for example, an accumulator, which is electrically connected to the electronics assembly 3 to supply the electronics assembly 3. The energy storage 4 is for example a lithium-ion accumulator, which can be recharged. Another solution for an energy storage would be, for example, a capacitor with an extremely low self-discharge. (e.g., gold cap).

As an element that is essential to the invention, the cardiac pacemaker 1 has a charging impulse generation portion 5 through which the energy storage 4 can be recharged again. The charging impulse generation portion 5 makes it possible to charge the energy storage 4 wirelessly.

The charging impulse generation portion 5 comprises, as essential elements, at least an impulse wire or Wiegand wire 51, which is axially surrounded by a coil 52 and which is wound around the coil 52, respectively, and charging electronics 53.

The impulse wire or Wiegand wire 51 forms a magnetization portion, which can be influenced by a changing externally generated magnetic field. Preferably the magnetization portion 51 may comprise a plurality of impulse wires and/or Wiegand wires, wherein each of the wires or a plurality of the wires may be surrounded by one or more coils.

The changing magnetic field is generated, for example, by a charging device, which will be explained below.

The magnetization portion 51 comprises evenly oriented magnetic domains which, when the magnetic field changes, start to remagnetize their polarities (to flip polarities) when a certain amplitude and field strength in the range of a few millitesla, respectively, is reached. From a physical aspect, this causes a remagnetization wave (Bloch wall) to run across the magnetization portion. In the literature, this event is also referred to as the big Barkhausen jump (großer Barkhausen-Sprung).

The size and speed of the remagnetization wave does not depend on the frequency (commutation frequency) with which the externally generated magnetic field changes. The remagnetization wave that runs across the magnetization portion generates a voltage impulse in the coil(s) 32 wound around the magnetization portion 51.

The voltage impulse is preferably processed by the charging electronics 53. The charging electronics 53 comprise for example a rectifier to rectify the voltage impulses of the coil(s), which are alternatingly generated with respective reverse polarities, and preferably a capacitor (for example a gold cap) to temporarily store electrical energy.

The charging electronics 53 ultimately emit a charging impulse to the energy storage 4, which charges the same.

The electronics assembly 3 may preferably be designed to output an Aus signal, which indicates the quality of the charging impulse emitted by the charging electronics 53. The electronics assembly 3 detects, for example, the strength of the charging impulse and generates the Aus signal on its basis. The Aus signal is outputted, for example, as a low-frequency radio signal. The Aus signal is processed by the charging device still to be explained below.

The electronics assembly 3, the energy storage 4, and the charging impulse generation portion 5 are together accommodated in a case 6 and are completely enclosed by the same. The case 6 is preferably made from titanium or a corresponding alloy and is therefore extremely suitable for implantation into the human body because no rejection reactions occur and, as a metallic body, it keeps away high-frequency interfering fields. The metallic body may furthermore be used as the ground electrode and the mass potential, respectively, that is necessary for the current impulse, which would not be possible with a glass body, for example. In the case of a not electrically conductive case, as for example with the mentioned glass body, the mass potential may be formed by an electrically conductive portion exposed on an outer surface of the case, or by a separate mass (cable) electrode.

Figure 2:
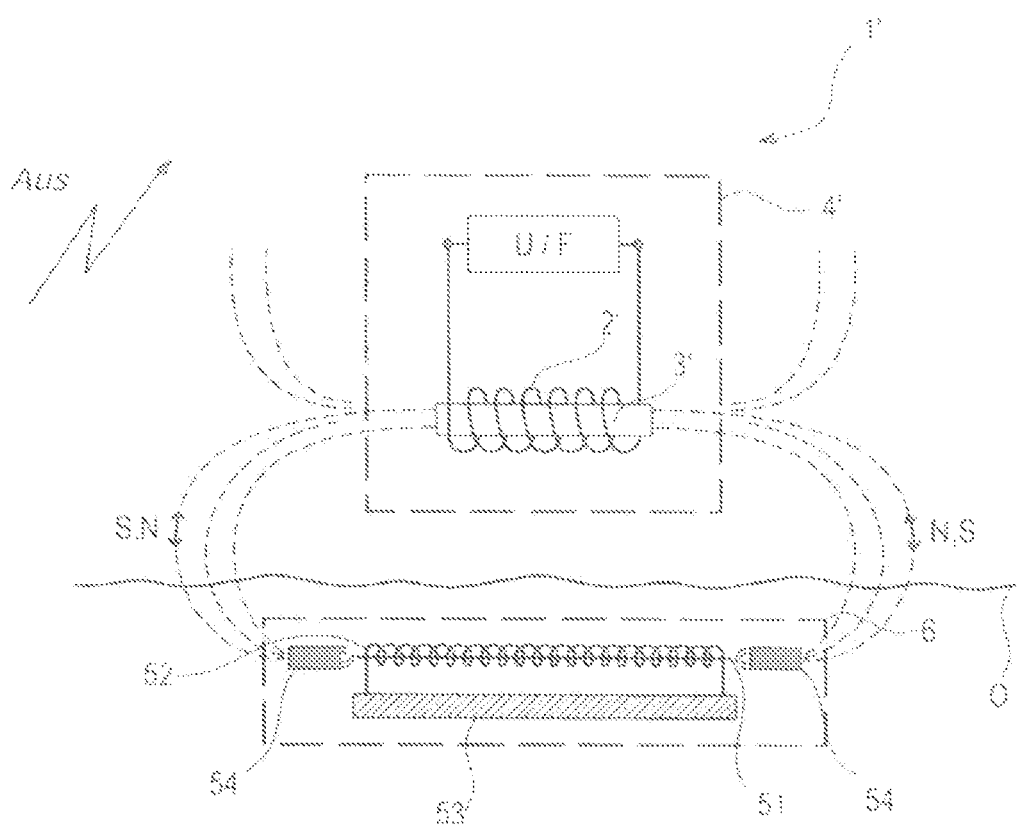
FIG. 2 shows a schematic illustration of a corresponding charging device.

FIG. 2 shows the schematic configuration of a charging device 1' according to the invention, which is used to recharge the electronic pacemaker 1.

According to the invention, the invention generally uses an indirect induction method to recharge the energy storage 4, which means that the energy is not transmitted, as in the direct induction, directly and without delay from a primary coil to a secondary coil (transformer principle), but indirectly from a primary coil located in the charging device explained below, first to the energy-storing magnetization portion 51 and from there, with a delay, to the coils 52 surrounding the magnetization portion 51.

The charging device 1' comprises a coil (primary coil) 2', for example, the current and/or voltage of which can be controlled in amplitude and frequency. Preferably, the coil 2' has a ferromagnetic core 3', for example from ferrite, to amplify the field.

A case 4' accommodates the corresponding components of the charging device. The case 4', if used as intended, is temporarily arranged near to or on a surface O of the human body so that the external magnetic field generated by the primary coil 2' in the charging device reaches the magnetization portion 51.

When the charging device is operated, it generates, by means of the primary coil 2'', an changing magnetic field which forms part of the electromagnetic field generated by the primary coil 2'. The generated changing magnetic field commutates with a certain commutation frequency and reaches the magnetization portion 51. Each commutation leads, when a certain field strength is reached, to the initiation of the remagnetization wave, wherein the coil 52, which forms, in the indirect induction method mentioned above, the secondary coil, alternatingly generates positive and negative voltage impulses. The voltage impulses are, as already explained, processed by the charging electronics 53 so that the charging electronics 53 ultimately output the charging impulse to the energy storage 4.

One essential point of the invention is, as already mentioned, that the contactless energy transmission is not based on the fact that the changing magnetic field, generated by the charging device 1', is used directly for the voltage induction in the secondary coil 52, but indirectly, in that the corresponding energy of the magnetic field is temporarily stored in the magnetization portion 51 and then released quite suddenly when the re-magnetization wave is initiated, whereby the voltage impulse is generated in the secondary coil 52 by induction. For this reason, the commutation frequency may be adapted so that energy can be transmitted through the case 6 made from metal without any problems as well.

The strength and/or commutation frequency of the magnetic field and the electromagnetic field, respectively, generated by the primary coil 2', can be controlled in the charging device 1' in order to adapt the recharging of the energy storage 4 to the specific location of the pacemaker 1 in the body of the living being and to the necessary penetration depth, respectively, and in order to minimize the charge time. The controlling of the strength and/or commutation frequency of the magnetic field and the electromagnetic field, respectively, generated by the primary coil 2' is performed in the charging device 1' preferably on the basis of the Aus signal, which is output by the pacemaker. To this purpose, the charging device 1' has the corresponding receiving properties to receive the (radio) signal Aus.

Preferably, the pacemaker 1 comprises, in the longitudinal direction of the coil(s) 52 at the end portions of the magnetization portion 51, magnetic collecting lenses 54 to bundle the changing magnetic field. The magnetic collecting lenses 54 may preferably have the form of a hollow cylinder into which the impulse wire/Wiegand wire or the impulse wires/Wiegand wires are inserted.

Alternatively or additionally to the magnetic collecting lenses 54, the case 6 of the pacemaker 1 may be made of two assembled case portions. The case portions may be formed from ferromagnetic metals or be coated with such, wherein the orientation of the charging impulse generation portion 5 is selected within the case 6 so that the case portions function as additional or exclusive collecting lenses 54.

Per commutation of the changing external magnetic field, the remagnetization wave, which runs across the magnetization portion 51, is initiated, and ultimately one of the charging impulses to recharge the energy storage 4 is generated.

Figure 3:
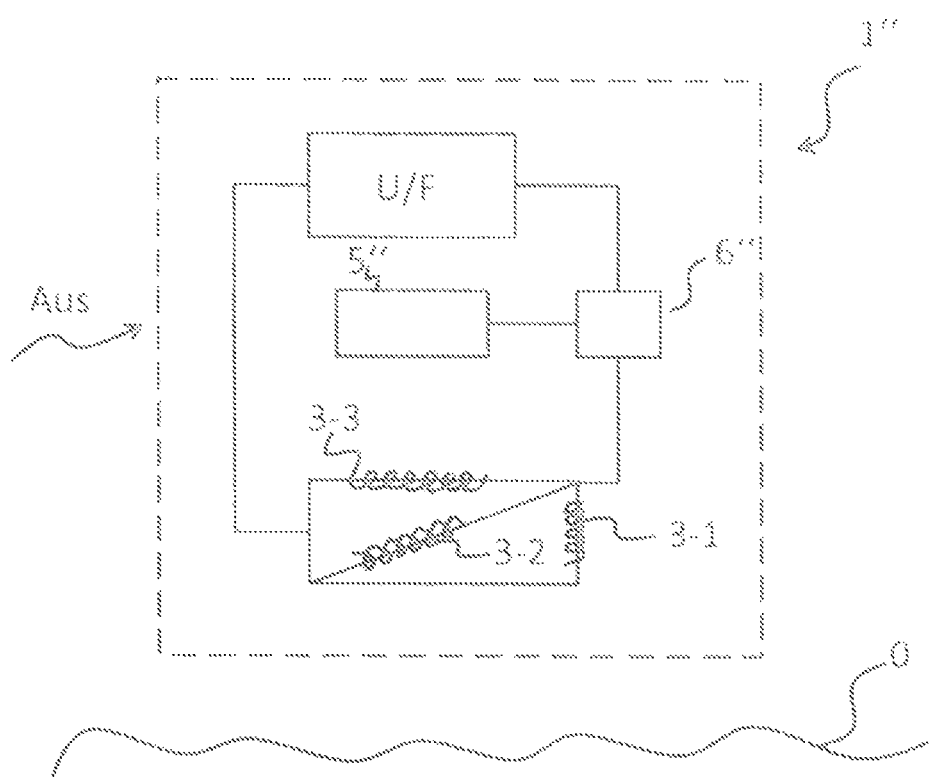
FIG. 3 shows an alternative configuration of the charging device shown in FIG. 2 with a plurality of coils.

FIG. 3 shows an alternative embodiment of a charging device 1" according to the invention.

The pacemaker is arranged as shown in FIG. 2 and is no longer shown in FIG. 3.

The charging device 1" shown differs from the one in FIG. 2 in that a plurality of coils 3-1, 3-2, 3-3, which respectively act as said primary coil, is provided. The charging device 1" preferably comprises an electronics assembly 5" and a multiplexer 6". The electronics assembly 5" is configured to control the multiplexer 6" and to determine in this manner which or in which combination the coils 3-1, 3-2, 3-3 are used to generate the magnetic field. The controlling of the coils 3-1, 3-2, 3-3 is based on the (radio) signal Aus from the pacemaker 1, which indicates the quality of the charging impulse.

The coils 3-1, 3-2, 3-3 are spatially arranged differently, whereby the orientation of the magnetic field may be altered to improve and optimize the charging impulse.

Each of the coils 3-1, 3-2, 3-3 preferably comprises a core as shown in FIG. 2 and inserted in coil 2'.

The invention claimed is:

1. An electronic cardiac pacemaker for implantation in a body of a living being and for controlling a heartbeat of a heart of a living being, wherein the pacemaker comprises:
   an electrode portion comprising at least one electrode;
   an electronics assembly connected with the electrode portion, configured to
      a. monitor the heartbeat of the heart to acquire body data, wherein the electronic assembly is able, through the body data, to determine whether the heartbeat needs to be controlled,
      b. generate a voltage impulse, if required, and
      c. emit the same via the electrode portion to the heart of the living being to control the heartbeat;
   an energy storage to supply the electronics assembly with electrical energy which can be recharged with electrical energy after discharge, wherein the energy storage is an accumulator; and
   a charging impulse generation portion electrically connected to the energy storage, which is configured to emit a charging impulse to the energy storage for the recharging of the energy storage;
   wherein
   the charging impulse generation portion comprises a magnetization portion with oriented magnetic domains which can be contactlessly influenced by an external magnetic field reversing with a reversing frequency, so that, when a certain field strength is respectively reached, a remagnetization wave, caused by the continuously reversing magnetic domains, is initiated in the magnetization portion which runs across the magnetization portion and leads to the generation of the charging impulse
   wherein
   said electronic assembly together with said energy storage and said charging impulse generation portion are completely surrounded by a housing formed of a material which is not repelled by the body of the living being, and said at least one electrode is formed on an outer surface of said housing,
   the cardiac pacemaker is configured to be implanted, as intended, into the heart or attached to an external surface of the heart, and the electrode formed on the external surface is configured to be brought into contact with and/or anchored to the heart as intended, and
   the accumulator is to be charged as intended by generating the external magnetic field.

2. The electronic cardiac pacemaker according to the claim 1, wherein the charging impulse generation portion comprises at least one coil which is spatially arranged to the magnetization portion, so that it generates a voltage impulse, which leads to the charging impulse, when the remagnetization wave occurs.

3. The electronic cardiac pacemaker according to claim 2, wherein the magnetization portion is configured by mechanical machining so that the magnetic domains of the magnetization portion are equally oriented.

4. The electronic cardiac pacemaker according to claim 3, wherein the magnetization portion of the electronic pacemaker comprises a magnetically hard shell area which encloses a magnetically soft core area.

5. The electronic cardiac pacemaker according to claim 2, wherein the at least one coil surrounds the magnetization portion axially.

6. The electronic cardiac pacemaker according to claim 2, wherein the charging impulse generation portion of the pacemaker according to the invention comprises, in a direction in which the at least one coil is wound or in which the coils are wound, a magnetic collecting lens at least one end portion of the magnetization portion for bundling and guidance of the changing externally generated magnetic field to the magnetization portion.

7. The electronic cardiac pacemaker according to claim 6, wherein the at least one magnetic collecting lens is formed from ferromagnetic metal which bundles the magnetic field for the magnetization portion.

8. The electronic cardiac pacemaker according to claim 6, wherein the material is titanium, or a metal alloy comprising titanium.

9. The electronic cardiac pacemaker according to claim 1, wherein the magnetization portion is at least an impulse wire or a Wiegand wire.

10. The electronic cardiac pacemaker according to claim 9, wherein the magnetization portion comprises a plurality of impulse wires or a plurality of Wiegand wires or a combination of at least one impulse wire and one Wiegand wire.

11. The electronic cardiac pacemaker according to claim 10, wherein the coil is wound around the plurality or the combination of wires, or several coils are provided which are each wound around at least one of the wires.

12. The electronic cardiac pacemaker according to claim 1, wherein the material is a non-ferromagnetic metal.

13. The electronic cardiac pacemaker according to claim 1, wherein the electronics assembly and/or the charging impulse generation portion, except for the magnetization portion and, when provided, at least one magnetic collecting lens, does not comprise any elements from ferromagnetic materials.

14. The electronic cardiac pacemaker according to claim 1, wherein the electronics assembly of the electronic pacemaker is configured to send out a signal that indicates the quality of the charging impulse.

15. The electronic cardiac pacemaker according to claim 1, wherein the accumulator is, a lithium-ion accumulator.

* * * * *